United States Patent [19]

Aspden et al.

[11] Patent Number: 5,292,481
[45] Date of Patent: Mar. 8, 1994

[54] CRACK PROPAGATION TEST SPECIMEN

[75] Inventors: Robert G. Aspden, Export; Thomas G. Bengel, Plum Borough, both of Pa.

[73] Assignee: Westinghouse Electric Corp., Pittsburgh, Pa.

[21] Appl. No.: 15,962

[22] Filed: Feb. 8, 1993

[51] Int. Cl.$^5$ .................. G01N 17/00; G01N 17/04
[52] U.S. Cl. ........................ 422/53; 73/53.01; 73/104; 73/785; 73/799; 436/6
[58] Field of Search .............. 73/53.01, 61.62, 86, 73/104, 799, 819, 856, 859, 785; 422/53; 269/234, 254 R; 411/75, 76, 354; 203/7; 436/6

[56] References Cited

U.S. PATENT DOCUMENTS

| 3,116,117 | 12/1963 | Marsh et al. | 422/53 |
| 4,267,148 | 5/1981 | Dickson et al. | 422/53 |
| 5,147,802 | 9/1992 | Aspden et al. | 436/6 |

FOREIGN PATENT DOCUMENTS

| 2-272347 | 11/1990 | Japan | 422/53 |
| 932374 | 5/1982 | U.S.S.R. | 422/53 |
| 1065721 | 1/1984 | U.S.S.R. | 73/799 |
| 1193531 | 11/1985 | U.S.S.R. | 422/53 |
| 1259135 | 9/1986 | U.S.S.R. | 73/799 |
| 926561 | 5/1992 | U.S.S.R. | 73/799 |

OTHER PUBLICATIONS

H. R. Copson et al. *Corrosion* 1960, 16, 123–129.
H. L. Craig et al. Ing "Handbook on Corrosion Testing and Evaluation".
W. H. Ailor, Ed., John Wiley and Sons, Inc., New York, 1971, 231–271.
"Corrosion Basics An Introduction Duction" National Association of Corrosion Engineers, Houston, Tex., 1984, 309–317.

*Primary Examiner*—James C. Housel
*Assistant Examiner*—Arlen Soderquist
*Attorney, Agent, or Firm*—J. C. Valentine

[57] ABSTRACT

A crack propagation test specimen has a base metal and a clad metal. The base metal has an upper surface and a bottom surface with a hole extending from the bottom surface toward the upper surface. The cladding metal is supported on the upper surface of the base metal and has a first slot cut therethrough which is in fluid flow communication with the hole in the base metal. A second slot is cut in the cladding metal adjacent to the first slot for receiving a wedge. The first slot and the second slot define a wall which closes over the first slot when a wedge is forced into the second slot to simulate a hairline crack. A mechanically deformed metal sample is disposed in the hole in the base metal to simulate a stressed base metal supporting a cladding metal subject to hairline cracking.

5 Claims, 1 Drawing Sheet

CRACK PROPAGATION TEST SPECIMEN

BACKGROUND OF THE INVENTION

1. Field of the Invention

The present invention relates to the field of test specimens for evaluating crack propagation due to corrosion. More specifically, the invention relates to a unique apparatus for testing the effects of a corrodant upon a stressed base metal underlying a cladding metal.

2. DESCRIPTION OF THE PRIOR ART

The problem of excessive personnel exposures caused by high background radiation levels in a nuclear reactor primary system, such as in pressurized water reactor (PWR) systems, and the resultant economic cost of requiring personnel rotation to minimize individual exposure is significant at many nuclear plants. These background levels are principally due to the buildup of corrosion products in certain areas of the plant. The buildup of corrosion products exposes workers to high radiation levels during routine maintenance and refueling outages. The long term prognosis is that personnel exposure levels will continue to increase.

As a nuclear power plant operates, the surfaces in the core and primary system corrode. Corrosion products, referred to as crud, are activated by transport of the corroded material to the core region by the reactor coolant system (RCS). Subsequent release of the activated crud and redeposition elsewhere in the system produces radiation fields in piping and components throughout the primary system, thus increasing radiation levels throughout the plant. The activity of the corrosion product deposits is predominately due to Cobalt 58 and Cobalt 60. It is estimated that 80–90% of personnel radiation exposure can be attributed to these elements.

One way of controlling worker exposure, and of dealing with this problematic situation, is to periodically decontaminate the nuclear steam supply system using chemicals, thereby removing a significant fraction of the corrosion product oxide films. Prior techniques had done very little to decontaminate the primary system as a whole, typically focusing only on the heat exchanger (steam generator) channel heads.

Two different chemical processes, referred to as LOMI (developed in England under a joint program by EPRI and the Central Electricity Generating Board) and CAN-DEREM (developed by Atomic Energy of Canada, Ltd.), have been used for small scale decontamination in the past. These processes are multi-step operations, in which various chemicals are injected, recirculated, and then removed by ion-exchange. Although the chemicals are designed to dissolve the corrosion products, some particulates are also generated. While these chemical processes had typically been used on only a localized basis, use of these chemical processes has now been considered for possible application on a large scale, full system chemical decontamination.

One phase in the development of satisfactory dilute chemical decontamination (DCD) systems, such as CAN-DEREM and LOMI processes, is the study of the corrosive effects of DCD solutions on the materials and components in the RCS. There are components in the RCS that consist of carbon steel cladded with stainless steel on the exposed side. Thermal and mechanical stresses may cause small cracks to develop in the stainless steel cladding of these components.

Since it is known that these cracks exist, it is necessary to determine the corrosive effects of the DCD solutions which might penetrate through the cracks during the decontamination process. If the DCD solutions are corrosive in nature, they may impair the integrity of the underlying carbon steel.

U.S. Pat. No. 5,147,802, which issued Sep. 5, 1992 to the assignee of the present invention, generally discloses a very useful test specimen for evaluating crack propagation in a metal underlying a cladding metal subject to hairline cracking. However, this test specimen does not provide a means for evaluating the effect of penetrating corrodant upon a stressed base metal.

SUMMARY OF THE INVENTION

It is an object of the present invention to provide a means for evaluating the effect of a clad-penetrating corrodant upon a stressed base metal. It is another object of the present invention to provide a means for evaluating such an effect where corrodant penetrates through a hairline crack in the cladding metal.

With these objects in view, the present invention relates to a crack propagation test specimen having a cladding metal on a base metal. The base metal has an upper surface and a bottom surface with a hole extending from the bottom surface toward the upper surface. The cladding metal has a first slot cut therethrough which is in fluid flow communication with the hole in the base metal. A second slot is cut in the cladding metal adjacent to the first slot for receiving a wedge. The adjacent slots in the cladding metal define a yieldable wall which closes over the first slot to simulate a hairline crack when a wedge is forced into the second slot. A mechanically stressed metal sample is disposed in the hole in the base metal which communicates with the first slot in the cladding.

In a preferred embodiment, the stressed metal sample has a U-bend shape, which may be created by forcing a substantially flat sample into the hole with a mandrel. Advantageously, the hole of the base metal into which the mandrel forces the sample functions a die member and as a sample holder. Also, the elasticity of the deformed metal sample will urge the ends of the deformed sample against the sidewalls of the hole in the base metal so that the ends of the sample are yieldably restrained and the sample is firmly maintained in place in the assembly.

BRIEF DESCRIPTION OF THE DRAWINGS

The invention as set forth in the claims will become more apparent from the following detailed description of two preferred embodiments thereof shown, by way of example only, in the accompanying drawings, wherein:

DESCRIPTION OF THE PREFERRED EMBODIMENT

Figure 1:
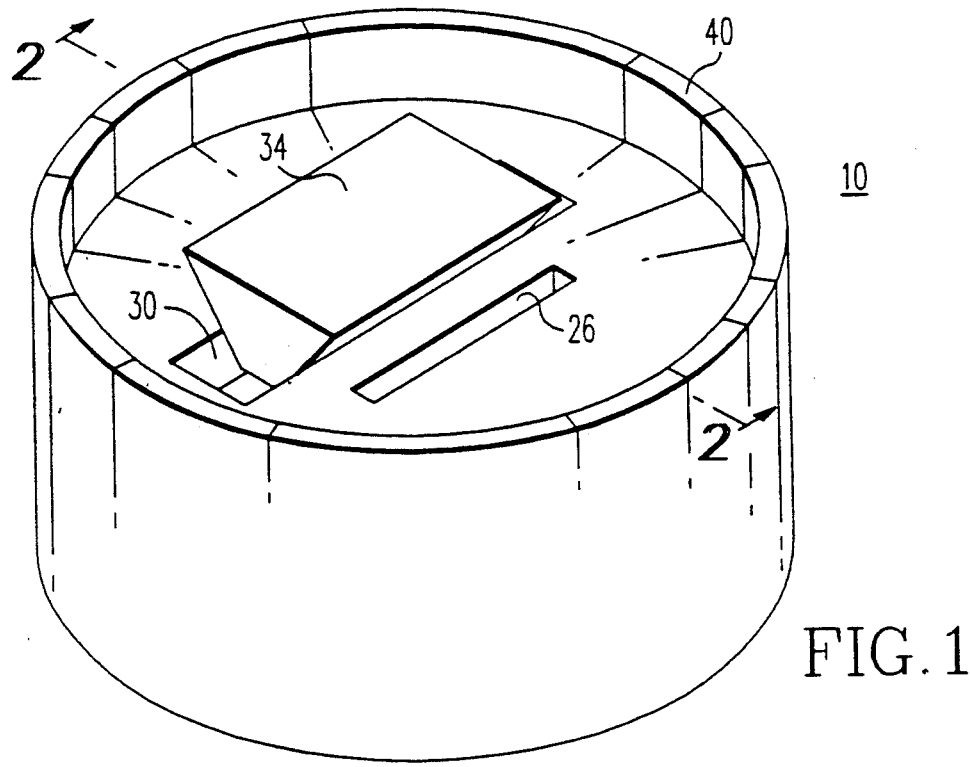
FIG. 1 is a perspective view of a test specimen embodying the present invention.
Figure 2:
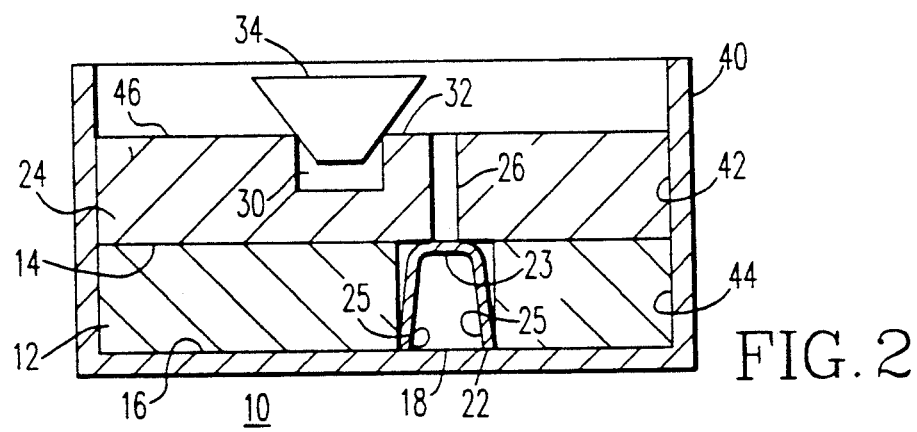
FIG. 2 is an enlarged cross sectional view of the test specimen of FIG. 1 taken along section line 2—2.
Figure 3:
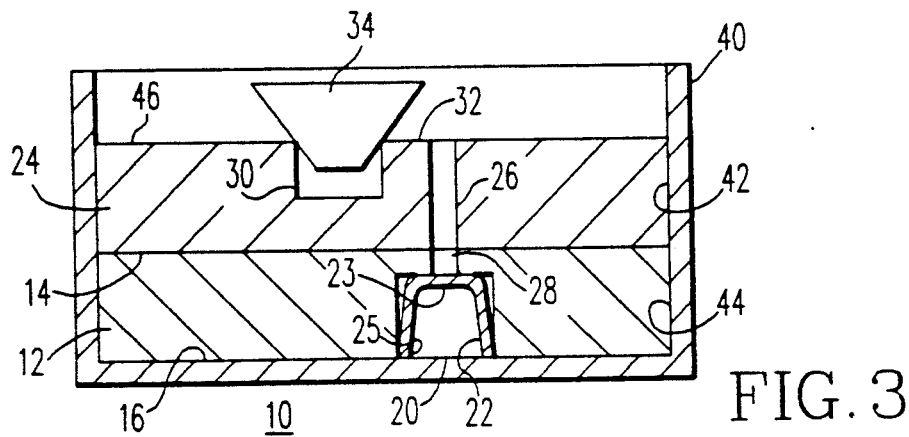
FIG. 3 is an enlarged cross sectional view similar to FIG. 2 and taken along section line 2—2 showing a second preferred embodiment of the present invention.

Referring now to the drawings in detail, FIG. 1 generally shows a test specimen 10 similar to the test specimen of U.S. Pat. No. 5,147,802, the structure of which is hereby incorporated by reference. A base metal 12 has an upper surface 14 and a lower surface 16, as is shown in the alternative embodiments of FIGS. 2 and 3. The base metal 12 also has a hole such as a hole 18 (extending entirely therethrough up to the upper surface 14 as shown in FIG. 2) or a hole 20 (extending in spaced relationship to the upper surface 14 as shown in FIG. 3) extending from the bottom surface 16 of the base metal 12. Hole 18 and hole 20 may have any suitable shape, but preferably are generally rectangular slots for receiving a rectangularly shaped strip sample 22 as is discussed below.

A cladding metal 24 is disposed on the upper surface 14 of the base metal 12. The cladding metal 24 has a first slot 26 cut therethrough such that the first slot 26 communicates with the hole 18 or 20 in the base metal 12. FIG. 2 shows a first slot 26 which communicates with the hole 18 at the upper surface of the base metal. FIG. 3 shows a first slot 26 communicating with hole 20 via a slot 28 which may be cut into the base metal 12 at the time slot 26 is cut. In embodiments simulating cladded carbon steel vessels and piping of nuclear and chemical plants where the base metal 12 is carbon steel and the cladding metal 24 is stainless steel, the first slot 26 is preferably cut by electrical discharge machining ("EDM"). EDM techniques have the ability to cut a crack slot with a width from about 0.13 mm to about 0.37 mm (0.005 in to 0.02 in) to practically any depth.

The cladding metal 24 also has a second slot 30 cut therein adjacent to the first slot 26. The two slots 26 and 30 define a wall 32 which at least partially closes over the first slot 26 to simulate a hairline crack when a wedge 34 is forced into the second slot 30. The wedge 34 as shown in FIGS. 2 and 3 is in a preliminary position before being forced into the second slot 30 to close the yieldable wall 32 over the first slot 26 to simulate a hairline crack. The second slot 30 may be cut to any suitable depth, but it preferably does not extend through the cladding metal 24. Thus, for example, where a hairline crack is to be simulated in a stainless steel cladding metal, a shallow slot 30 may be cut to a depth of about 0.06 in with nominal dimensions of 0.5 in. long×0.12 in. wide. The closing wall 32 may have a nominal width of 0.015 in. A wedge may then be forced into the second slot 30 to close the wall 32 over the first slot 26 to simulate a hairline crack having a width of from about 0.0005 in. to about 0.0015 in. or more.

The mechanically stressed sample 22 may be positioned in the hole 18 or the hole 20 by any suitable means. In a preferred practice where a stressed carbon steel composition is to be evaluated, a flat strip having nominal dimensions of 1.2 in.×0.25 in.×0.015 in. is placed over the hole I and a mandrel (not shown) is employed to deform the strip into a U-bend shape (having, e.g., a ⅛ in. radius in the bend 23 and ½ in. extensions 25) and to force the U-bend shape into the hole. Thus, the base metal 12 with the hole 18 or hole 20 functions as a die member for shaping the sample 22. The effects of corrodant upon different stress levels may be determined by serially testing several similarly dimensioned flat strip samples which have been forced into the hole 18 or the hole 20 with mandrels having different diameters whereby different bend configurations having different stress patterns are developed in the samples 22. Also, the effects of corrodant upon several stress levels of the same metal may be determined by serially testing samples of different thicknesses in the die, i.e., hole 18 or hole 20. Advantageously, the elasticity in the metal sample 22 urges the ends of the extensions 25 of the sample 22 against the sidewalls of the hole 18 or the hole 20 so that the sample 22 remains in position while the die functions as a sample holder during the corrosion test. The sample 22 will normally have the same composition as the base metal 12. However, the sample 22 may have a composition which is different from the base metal 12 where, for example, a previously employed test specimen is used as a standard to evaluate a different base metal composition having different stress levels. Thus, for example, several different carbon steel or stainless steel U-bend samples having different levels of stress may be serially evaluated in the same assembly.

The entire specimen may be fitted into a Swagelok tube cap assembly 40 or other holder which encases at least a portion of the sides 42 of the cladding metal 24 and the sides 44 and the bottom surface 16 of the base metal 12 to prevent short-circuiting of the corrodant solution around the simulated crack 26 and direct access to the sample 22.

In a preferred practice of the present invention, a sample 22 is forced into the hole 18 or 20 by the axially extending surface of a generally circular mandrel (not shown) and the assembly is encased in a holder 40. A wedge 34 is then forced into the second slot 30 to close wall 32 over the first slot 26 to simulate a hairline crack. Alternatively, the wedge 34 may be installed before the assembly is encased in the holder 40. Thus, corrodant penetration through a hairline crack to an adjacent stressed material may be accurately simulated.

While preferred embodiments of the present invention has been shown and described, it is to be understood that the invention may be otherwise variously embodied within the scope of the following claims of invention.

We claim:
1. A crack propagation test specimen comprising:
   a base metal having an upper surface and a bottom surface, and a hole extending from the bottom surface toward the upper surface;
   a cladding metal on the upper surface of the base metal, the cladding metal having a first slot cut therethrough, the first slot in fluid flow communication with the hole in the base metal, and having a second slot cut therein adjacent to the first slot for receiving a wedge, the first slot and the second slot defining a wall which closes over the first slot when a wedge is forced into the second slot;
   a mechanically deformed metal sample disposed in the hole in the base metal; and
   a specimen holder which encases the base metal and at least a portion of the cladding metal.
2. The crack propagation test specimen of claim 1, wherein the mechanically deformed metal sample has a U-bend shape with extending ends yieldably restrained by the hole.
3. The crack propagation test specimen of claim 1, wherein the mechanically deformed U-bend sample has an arcuate portion adjacent the cladding.
4. The crack propagation test specimen of claim 1, wherein the mechanically deformed U-bend sample has an arcuate portion spaced from the cladding metal.
5. The crack propagation test specimen of claim 1, wherein the metal sample is deformed by:
   placing a substantially flat sample against the bottom surface of the base metal and over the hole therein; and
   forcing the flat sample into the hole with a mandrel.

* * * * *